(12) United States Patent
Hayden et al.

(10) Patent No.: US 7,310,142 B2
(45) Date of Patent: Dec. 18, 2007

(54) FAST TIME-CORRELATED MULTI-ELEMENT PHOTON DETECTOR AND METHOD

(75) Inventors: Carl C. Hayden, Dublin, CA (US); David W. Chandler, Livermore, CA (US); A. Khai Luong, Dublin, CA (US)

(73) Assignee: Sandia National Laboratories, Livermore, CA (US)

( * ) Notice: Subject to any disclaimer, the term of this patent is extended or adjusted under 35 U.S.C. 154(b) by 277 days.

(21) Appl. No.: 11/209,353

(22) Filed: Aug. 22, 2005

(65) Prior Publication Data

US 2007/0041011 A1    Feb. 22, 2007

(51) Int. Cl.
*G01J 3/30* (2006.01)
(52) U.S. Cl. ..................................... 356/318
(58) Field of Classification Search ................. 356/318
See application file for complete search history.

(56) References Cited

U.S. PATENT DOCUMENTS 4,242,700 A * 12/1980 Weimer ...................... 348/275
6,687,000 B1 * 2/2004 White ......................... 356/328

FOREIGN PATENT DOCUMENTS

DE    4339787 C2    5/1995

OTHER PUBLICATIONS

Becker & Hickl GmbH, PML-16 16 Channel Photomultiplier Head Product Information, no date provided.

* cited by examiner

*Primary Examiner*—Gregory J. Toatley, Jr.
*Assistant Examiner*—Kara Geisel
(74) *Attorney, Agent, or Firm*—Dorsey & Whitney LLP

(57) ABSTRACT

Photons emitted from a sample responsive to being excited by laser pulses are directed through a prism onto a photomultiplier tube having several spaced-apart anodes. The prism alters the path of each photon as a function of its wavelength so that the wavelength determines the anode to which the photon is directed. Taps of first and second delay lines that are coupled to respective alternating anodes. When an anode receives the photon, it generates a pulse that propagates through the delay line in opposite directions from its associated tap. A timer determines first and second times from the laser pulse to the pulse reaching the first and second ends of the delay line. The difference between the first and second times corresponds to the wavelength of the emitted photon and the sum of the first and second times corresponds to the emission delay of the emitted photon.

35 Claims, 3 Drawing Sheets

FAST TIME-CORRELATED MULTI-ELEMENT PHOTON DETECTOR AND METHOD

STATEMENT REGARDING FEDERALLY-FUNDED RESEARCH

This invention was made with Government support under government contract no. DE-AC04-94AL85000 awarded by the U.S. Department of Energy to Sandia Corporation. The Government has certain rights in the invention, including a paid-up license and the right, in limited circumstances, to require the owner of any patent issuing in this invention to license others on reasonable terms.

TECHNICAL FIELD

This invention relates to a photon detector for measuring the wavelength and emission time of photons emitted by a sample that has been excited by a laser, and, more particularly, to a photon detector that can simultaneously perform both measurements at a high repetition rate.

BACKGROUND OF THE INVENTION

A wide variety of devices are used to study the property of materials. For example, confocal microscopes are often used to study the spectral characteristics of materials responsive to being excited by electromagnetic radiation, such as a laser pulse. In a conventional confocal microscope, light from an excitation laser is directed through an objective lens of the microscope, which focuses the light on a sample. Fluorescence from the sample is collected and imaged through a pinhole to eliminate light that does not originate from the focus of the laser in the sample. This improves the spatial resolution of the microscope. The fluorescence light that passes through the pinhole is detected and the signal recorded. To form an image of the sample, either the sample is scanned through the laser or the laser is scanned across the sample while the resulting fluorescence is detected and the signal recorded. In conventional confocal microscopes, structures in the (usually biological) sample are stained with fluorescent dyes. Dyes with different fluorescence characteristics have been developed along with methods of specifically attaching these dyes to particular structures. Identifying the dye, usually through the wavelength range of its fluorescence, thus identifies structures in the sample. Characteristics of the fluorescence such as the lifetime and spectrum contain additional information about the sample and distinguishing them can provide additional contrast in the image. An important challenge in applying confocal microscopy is the need to obtain as much information from the fluorescent dyes as possible before the dyes bleach from exposure to the exciting laser light. Conventional photon detectors are often incapable of providing sufficient information before excessive bleaching of the dyes has occurred.

A sample exposed to a moderate level of excitation, such as a laser pulse, may not emit a photon responsive to each laser pulse. Instead, the sample may emit a photon infrequently, such as one every 50 laser pulses. However, there is a finite probability that a photon will be omitted responsive to each laser pulse. The probability of emitting a pulse as a function of emission delay time is known as the "fluorescence lifetime." A typical fluorescence lifetime graph is shown in FIG. 1 in which the probability "P" of emitting a photon is plotted on the Y-axis and the time delay "$\tau$" between the excitation and the emission of a photon is plotted on the X-axis. As shown in FIG. 1, the probability of emitting a photon decreases as a function of time after the excitation pulse. FIG. 1 shows that, if the excitation pulse results in a photon being emitted, the photon is most likely to be emitted soon after the excitation pulse. Conversely, if a substantial time has lapsed since the excitation pulse without a photon being emitted, there is relatively little probability that a photon will be emitted from the sample at all.

In the past, it has been fairly difficult and time consuming to obtain sufficient data about a sample to determine its fluorescence lifetime and the wavelengths of its emitted photons. This difficulty is primarily due to the very small delay time between the excitation pulse and the emission of a photon. Typical delay times are on the order of 2-3 ns ($10^{-9}$ sec.), and delay time measurements should be made with resolutions on the order of 10-20 ps ($10^{-12}$ sec.). It can be very difficult to measure time periods of such small durations. The difficulty in obtaining sufficient data also results from the relatively few number of excitation pulses that result in a photon being emitted, coupled with the need to obtain data about a large number of emitted photons. Data for a large number of photons must be collected because the probability of emitting a photon at each delay time is determined by counting the number of photons emitted at each delay time. A larger sample provides more accurate results. As a result, the sample must be exposed to a very large number of excitation pulses to emit enough photons to make an accurate determination of fluorescence lifetime.

There are situations where the fluorescence lifetime depends on the wavelength. This relation between lifetime and wavelength will only be observed if the emission time and wavelength of each photon are simultaneously measured. The correlation between lifetime and wavelength of the fluorescence can supply additional information about the sample being observed. Various approaches have been used to determine the wavelengths and fluorescence lifetimes of photons emitted from samples. For example, photons emitted responsive to laser pulses have been coupled to photodetectors through bandpass filters that allow photons to pass only if they are within one or more narrow bands of wavelengths. However, this approach can provide data only if the wavelength(s) of the emitted photons is known. It may not provide accurate results if the wavelengths are not known, nor can it easily determine the wavelength of emitted photons is the photons are emitted at a large number of different wavelengths, such as an entire spectrum of wavelengths.

To detect changes in a sample, such as those caused by diffusion, it is important to obtain the fluorescence spectral and lifetime information rapidly compared to these changes. In practical situations this often requires the detection system to be capable of recording photons at rates of $1 \times 10^6$ photons/second or faster.

There is therefore a need for a device and method that is capable of simultaneously measuring the wavelengths and delay times of emitted photons, and doing so in a quick and easily manner, and in a manner that provides sufficient information about the sample before fluorescent dyes used in the sample have been excessively bleached.

SUMMARY OF THE INVENTION

A method and system for determining the wavelength and/or delay time of a photon emitted from a sample uses an electromagnetic source, such as a laser, that emits an excitation pulse, which is coupled to a sample along a first optical path. In response to the excitation pulse, the sample may emit a photon. The photon is directed to a photon detector along a second optical path that is altered as a function of the wavelength of the photon emitted from the sample. The photon detector includes a plurality of detector elements each of which generates an electrical pulse when a photon is incident on the detector element. The particular detector element generating the electrical pulse thus depends upon the wavelength of the photon. The detector elements are coupled to respective taps of a delay line. The electrical pulse from the detector element receiving the photon propagates from the tap to which it is connected in opposite directions along the delay line to first and second output terminals. Timers coupled to the output terminals determine respective first and second times corresponding to the lapses in time from the excitation pulse to the electrical pulses reaching the output terminals. A calculation device calculates the difference between the first and second times and/or the sum of the first and second times. The difference between the first and second times provides an indication of the wavelength of the emitted photon. The sum of the first and second times provides an indication of the emission delay of the emitted photon.

DETAILED DESCRIPTION

Figure 2:
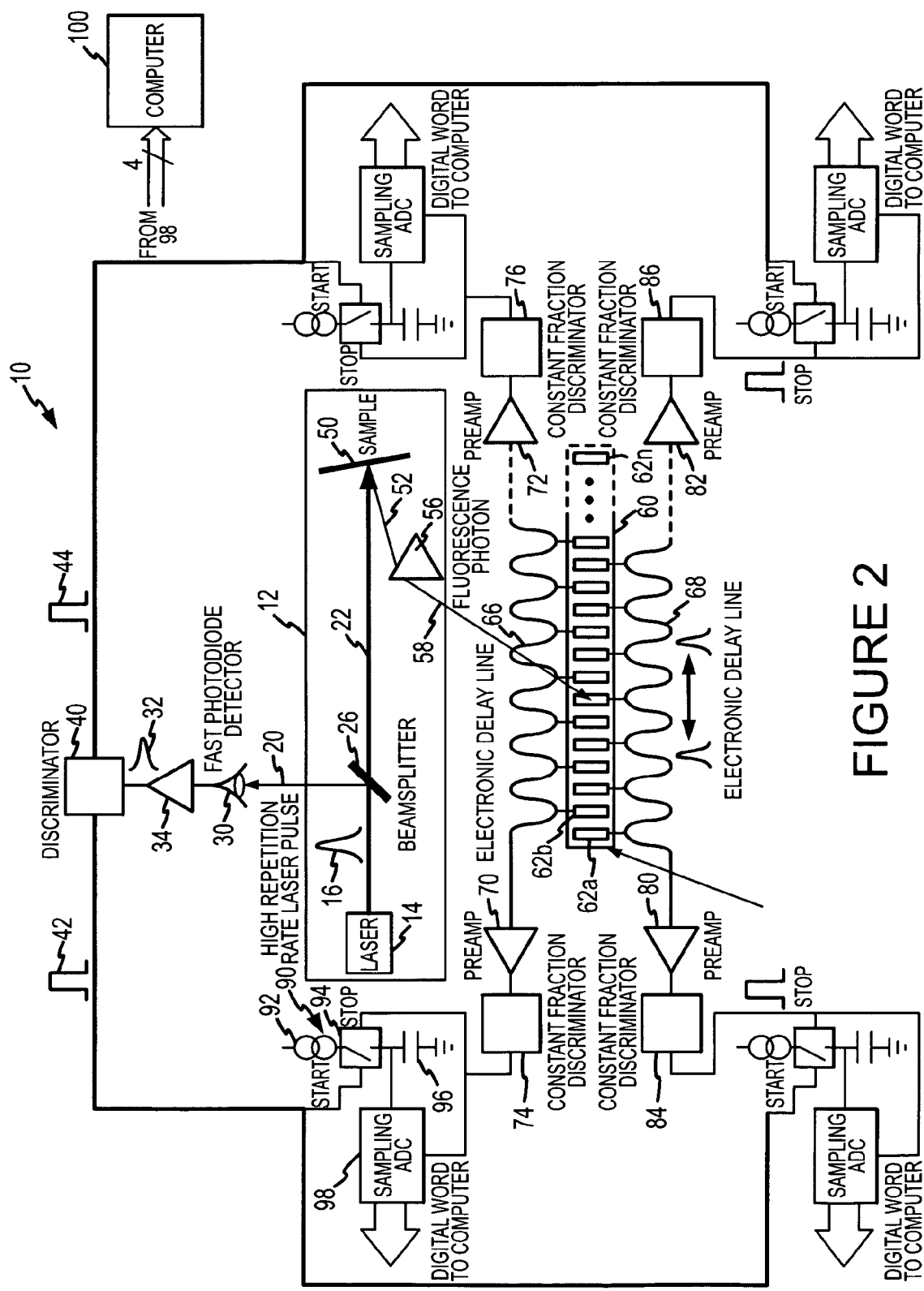
FIG. 2 is a block diagram of a system for measuring the wavelengths and emission delay times of photons emitted from a sample according to one embodiment of the present invention.

A photon detection system 10 for determining the wavelengths and delay times of photons emitted from a sample according to one embodiment of the invention is shown in FIG. 2. The system 10 and includes a sample excitation section 12 that includes a conventional pulsed laser 14 that periodically emits pulses 16 of coherent electromagnetic energy. The laser pulses 16 are divided into two paths 20, 22 by a beamsplitter 26. The laser pulse taking the first path 20 exits from the sample excitation section 12 and is received by a fast photodiode detector 30, which generates a corresponding electrical pulse 32 at the output of an amplifier 34. The electrical pulse 32 is applied to a discriminator 40, which is preferably a constant fraction discriminator. As is well-known in the art, a constant fraction discriminator generates an output pulse that switches states at an amplitude of an input signal that is a predetermined percentage of the maximum amplitude of the input signal. The constant fraction discriminator is thus insensitive to amplitude variations of the input signal. The discriminator 40 generates two identical pulses 42, 44 at the same time, which are used as "START" pulses in a manner that will be described below.

The second path 22 taken by the laser pulse 16 directs the pulse to a sample 50. When the sample 50 is excited by the laser pulse, there is a probability that a photon will be emitted, as previously explained. If a photon is emitted, it travels through a path 52 to a prism 56, which redirects the photon from the sample excitation section 12 along a path 58 corresponding to the wavelength of the photon. The redirected photon is incident on a photomultiplier tube 60 having a large number of the anodes 62a-n. The anode 62a-n to which the photon is redirected is thus determined by the wavelength of the photon. Alternating anodes 62a-n are coupled to respective taps of a pair of delay lines 66, 68 each having output terminals at opposite ends. The output terminals of the delay line 66 are coupled through respective preamplifiers 70, 72 to respective constant fraction discriminators 74, 76. Similarly, the output terminals of the delay line 68 are coupled through respective preamplifiers 80, 82 to respective constant fraction discriminators 84, 86. As explained above, the constant fraction discriminators 74, 76, 84, 86 generate a binary output that switches state responsive to an input signal transitioning through a voltage that is a predetermined percentage of the maximum amplitude of the input signal.

The outputs of the constant fraction discriminators 72, 76, 84, 86 are applied to respective integrators 90 each of which is formed by a constant current source 92 directing current through a switch 94 to a capacitor 96. An analog to digital converter ("ADC") 98 is coupled to capacitor 96 to output a digital signal indicative of the voltage on the capacitor 96. The respective digital words from the 4 ADCs 98 are coupled to a conventional computer 100, which is programmed to determine a wavelength and delay time of the photon based on the values of each digital word.

In operation, the laser 14 periodically generates pulses of laser radiation. In one embodiment, the laser pulses are generated at a frequency of 50 mHz. The portion of the laser pulse 16 following the path 20 causes the discriminator 40 to generate a pair of START pulses 42, 44. The "START" pulses 42, 44 cause the switch 94 in each of the integrators 90 to close thereby causing the voltage on the capacitor 96 to linearly increase. Although not apparent from FIG. 2, the START pulses also reset the voltages on the capacitors 96 prior to beginning with the integration.

At the same time, the portion of the laser pulse 16 following the path 22 may cause a single photon to be emitted from the sample 50, although photons are generally not emitted responsive to most of the laser pulses striking the sample 50. The probability of a photon being emitted could be increased, and might even approach unity, by increasing the intensity of the laser pulses, but doing so might require the intensity to be increased to the point where the sample might be damaged.

When a photon is emitted from the sample, it is redirected by the prism 56 to one of the anodes 62 of the photomultiplier tube 60 depending upon the wavelength of the photon. The anode 62 receiving the photon will then couple an electrical pulse to one of the delay lines 66, 68 through a tap corresponding to the location of the anode 62. The electrical pulse propagates through the delay line 66 or 68 in opposite directions. When the pulse reaches its respective constant fraction discriminator 74, 76, 84 or 86, the discriminator generates a "STOP" pulse. The STOP pulse opens the switch 94 in the respective integrator 90 so that the voltage on the capacitor 96 no longer to increases. As a result, the digital word from the ADC 98 corresponding to the voltage on the capacitor 96 provides an indication of the delay from the generation of the laser pulse to receipt of the resulting photon up at the photomultiplier tube 60 and the propagation of the resulting electrical pulse through the delay line 66 or 68 to the switch 94. More specifically, the total delay corresponding to the digital word from the ADC 98 is given by the following Equation 1:

$$TDC=PED+OD+DetD+TLD-SPD \quad [1]$$

where:
PED is the delay between the excitation laser pulse and the emission of the photon from the sample 50;
OD is the time required for the photon to travel from the sample 50 to the photomultiplier tube 60;
DetD is the time delay through the photomultiplier tube 60;
TLD is the propagation time of the electrical pulse from the anode 62 receiving the photon to one of the delay line output terminals; and
SPD is the delay time between the excitation laser pulse and the resulting
START signal reaching the switch 94 of the integrator 90.

The difference in a delay value TDC0 of an electrical pulse from one terminal of a delay line 66 or 68 and a delay value TDC1 of the same electrical pulse from the other terminal of the same delay line 66 or 68 provides an indication of the location of the anode 62 receiving the photon. If, for example, the delay values TDC0 and TDC1 are identical to each other, then the photon was received by the anode 62 at the center of the photomultiplier tube 60. If the delay value TDC0 is much smaller than the delay value TDC1, then the photon was received by the anode 62 at one end of the photomultiplier tube 60. If, on the other hand, the delay value TDC1 is much smaller than the delay value TDC0, then the photon was received by the anode 62 at the other end of the photomultiplier tube 60. The difference between TDC0 and TDC1 thus provides an indication of the location of the anode 62 receiving the photon, which, as explained above, corresponds to the wavelength of the photon. The difference between TDC1 and TDC0 is given by the Equation 2:

$$TDC1-TDC0=[PED1+OD1+DetD1+TLD1-SPD1]-[PED0+OD0+DetD0+TLD0-SPD0]. \quad [2]$$

The above Equation 2 can be rearranged by combining like terms to the following Equation 3:

$$TDC1-TDC0=[PED1-PED0+OD1-OD0+DetD1-DetD0+TLD1-TLD0-SPD1+SPD0]. \quad [3]$$

The delay between the excitation laser pulse and the emission of the photon from the sample 50, i.e., PED, may vary from one photon to the next. However, for a given photon, PED1 is equal to PED0 since the photon is produced by only one laser pulse so that PED1–PED0 is equal to zero. For all photons, the time required for the photon to travel from the sample 50 to the photomultiplier tube 60, i.e., OD, will be essentially constant so that OD1–OD0 is zero. Similarly, for all photons the time delay through the photomultiplier tube 60, i.e., DetD, will be nearly constant so that DetD1–DetD0 will also be zero. Finally, for all laser pulses, the delay time between the excitation laser pulse and the delay time of the resulting START signal reaching the switch 94, i.e., SPD, will be the same so that SPD0–SPD1 will be zero. As a result, the above Equation 3 can be reduced to the following Equation 4:

$$TDC1-TDC0=TLD1-TLD0. \quad [4]$$

The quantity TDC1–TDC0 can be determined by the computer 100 based on based on the values of the digital words from the ADCs. This quantity is proportional to the distance from the center of the delay line 66 or 68 that the electrical pulse entered the delay line 66 or 68, i.e., the location of the anode 62, to the center of the delay line 66 or 68. The quantity TDC1–TDC0 will thus have one of several discrete values corresponding to the wavelength of the photon. The quantity TDC1–IDC0 will be positive if the anode 62 receiving the photon was located on one end of the photomultiplier tube 60, and it will be negative if the anode 62 receiving the photon was located on the other end of the photomultiplier tube 60.

The average value of TDC1 and TDC0, i.e., [TDC1+TDC0]/2, is given by the following Equation 5:

$$[TDC1+TDC0]/2=[PED1+OD1+DetD1+TLD1-SPD1]/2+[PED0+OD0+DetD0+TLD0-SPD0]/2. \quad [5]$$

For the reasons explained above, OD1 is essentially equal to OD0, DetD1 is nearly equal to DetD0, and SPD0 can be made to equal to SPD1 for all laser pulses and all photons. The sum of the time required for the electrical pulse to travel from one tap of the delay line 66, 68 to the one end of the delay line and the time required for the electrical pulse to travel from the same tap of the delay line 66 or 68 to the other end of the delay line, i.e., TLD1+TLD0, is simply the total delay of the delay line 66 or 68. The above Equation 5 can therefore be reduced to Equation 6 as follows:

$$[TDC1+TDC0]/2=[PED1]/2+[PED0]/2+K \quad [6]$$

where K is a constant for all laser pulses and all photons. This Equation 6 can be rewritten to Equation 7 as follows:

$$[TDC1+TDC0]/2=[PED1+PED0]/2+K. \quad [7]$$

In the above Equation 7, only the expression PED1 and PED0 will vary from one photon to the next. However, for each photon the value of PED1 will be equal to PED0. Thus, Equation 7 can be rewritten as the following Equation 8:

$$[TDC1+TDC0]/2=PED+K. \quad [8]$$

As explained above, the value PED is the delay between the excitation laser pulse and the emission of the photon from the sample 50. Thus, the delay times of emitted photons is simply one-half the sum of the times TDC1+TDC0 corresponding to the digital words from the ADCs 98.

Figure 1:
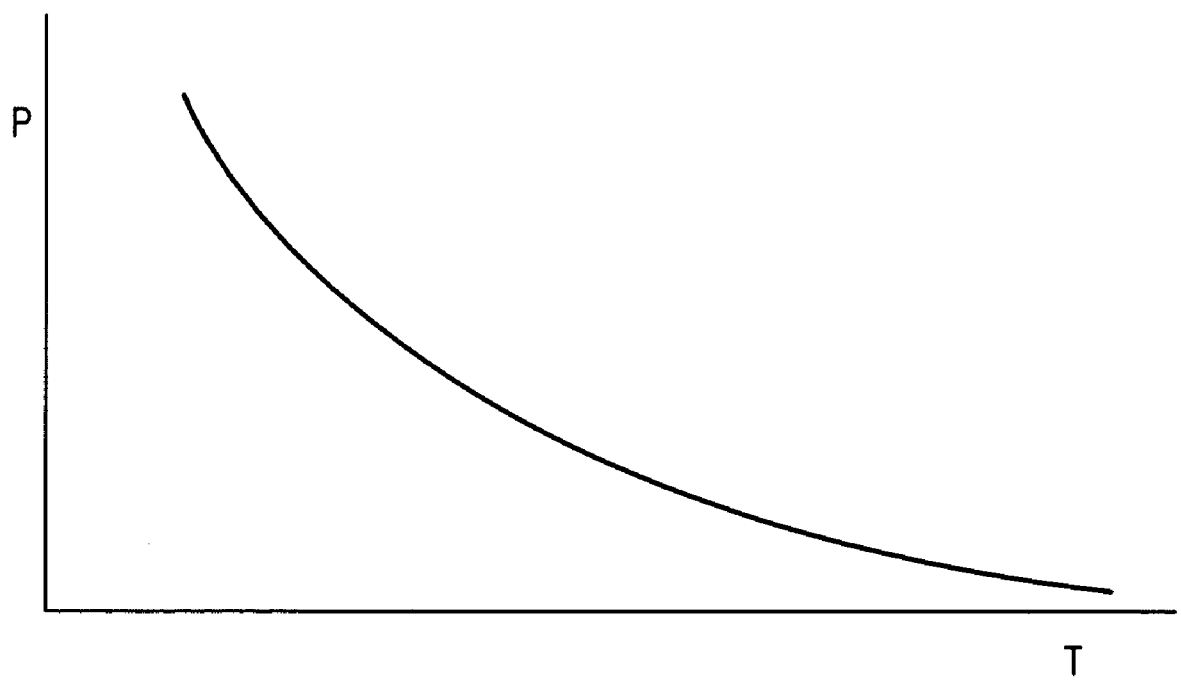
FIG. 1 is a graph showing a typical fluorescence lifetime for photons emitted from a sample.

The values PED for a large number of photons provides an indication of the probability of emitting a photon at each delay time after the sample is excited, and can be used to create a fluorescence lifetime graph of the type shown in FIG. 1. The system 10 of FIG. 1 thus allows the simultaneous measurement of both the wavelength of the photon and the delay in emitting the photon from the sample 50. Moreover, it allows such measurements to be performed very rapidly. For example, in one embodiment, the laser pulses are generated at a frequency of 50 mHz. If one photon is emitted for every 50 laser pulses, photons will be emitted and measurement data will be obtained at a rate of 1 mHz. At this rate, sufficient data can quickly be obtained to provide an accurate graph of fluorescence lifetime. Moreover, the wavelength of the photons can be recorded at the same time even if the wavelengths of the photons were not previously known.

As indicated above, the difficultly in obtaining fluorescence lifetime data stems from the very small increments of time involved in such data. For this reason, the design of the delay lines 66, 68 may be critical. The lengths of the delay lines 66, 68 should be sufficiently short that an electrical pulse coupled to one of their taps will propagate to the integrators 90 before the next laser pulse is generated. However, there must be a sufficient delay between adjacent taps to provide good resolution from one tap to the next. If the delay increment between adjacent taps is too small, it may be difficult to identify the tap to which the electrical pulse is coupled, which would make it difficult to identity the anode 62 receiving the photon. Resolution can be improved without increasing the total delay of the delay lines 66, 68 by connecting the taps of one delay line 66 to alternating anodes 62, and connecting the taps of the other delay line 68 to the remaining anodes 62. In one embodiment, the delay increment from one tap to the next of each delay line 66, 68 is 0.5 ns. If, for example, the photomultiplier tube 60 has 100 anodes 62, each delay line 66, 68 will have 50 taps connected to 50 alternating anodes 62. The total delay of the delay line 66, 68 would then be 25 ns, i.e., 50*0.5 ns. If a single delay line was used instead, the single delay line would need 100 taps to connect to the 100 anodes 62. If a delay resolution of 0.5 ns between taps was maintained, the total delay of the delay line would be 50 ns, i.e., 100*0.5 ns. Under these circumstances, the repetition rate of the laser 14 would be more limited. Delay resolutions can be further improved without increasing the total delay of delay lines 66, 68 by using additional numbers of delay lines, and alternating the connections between the anodes 62 and the taps of the delay lines. For example, in one alternative embodiment, 4 delay lines are used, and the taps of each of the delay lines are connected to every fourth anode 62. As explained above, in the system 10 of FIG. 2, it is necessary to reset the voltages on the capacitors 96 responsive to each START pulses. This procedure is necessary because the capacitors 96 will begin integrating responsive to each laser pulse, but they will not stop integrating until a photon is emitted. However, what is desired is for the integration to occur only during the period between a laser pulse that results in the emission of the photon and the emission of that photon. The need to reset the capacitors 96 in this manner can be avoided in an alternative embodiment in which the outputs of the constant fraction discriminators 74 are coupled to the START inputs of a respective integrator 90, and the outputs of the discriminator 40 are coupled to the STOP inputs of a respective integrator 90. Using this arrangement, integration will not start until a photon is produced, and it will stop when the next laser pulse is generated. As a result, it is only necessary to reset the voltage on the capacitors 96 when a photon is emitted. As long as the laser pulses are generated at a constant frequency, the period from the previous laser pulse that resulted in the photon emission and the emission of that photon can be determined. More specifically, the desired delay time can be determined by simply subtracting the delay time corresponding to the digital words from the ADCs 98 from the period between successive laser pulses. Other variations for determining the correct time delay will be apparent to one skilled in the art.

The photon detection system 10 is able to obtain substantial additional information that is not measured by conventional photon detectors from the fluorescent dyes in the sample 50 before the dyes bleach from exposure to the exciting light from the laser 14. Further, the photon detection system 10 records the entire fluorescence spectrum and associated lifetime simultaneously and continuously. In addition, the simultaneous measurement of emission time and wavelength for each photon provides information on the correlation between the fluorescence wavelength and lifetime that is not available from other methods of spectral and lifetime measurement. As a result, multiple dyes fluorescing at different wavelengths can be detected at the same time without having to rescan the sample 50.

Figure 3:
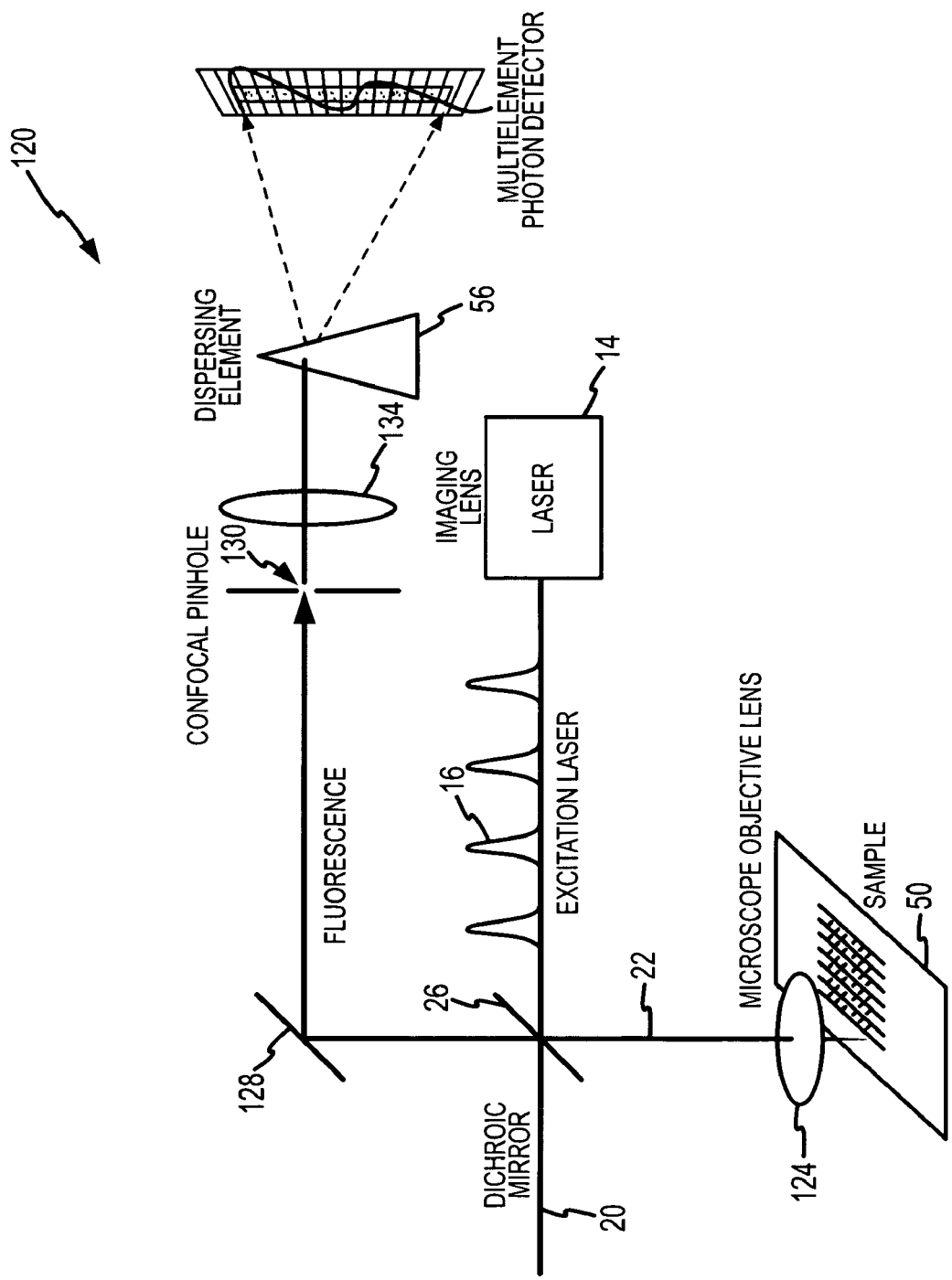
FIG. 3 is a block diagram of a system for measuring the wavelengths and emission delay times of photons emitted from a sample according to another embodiment of the invention in which a sample excitation section is incorporated in a confocal microscope.

The system 10 shown in FIG. 2 can be adapted to use in a confocal microscope by replacing the sample excitation section 12 in the system 10 of FIG. 2 with a confocal microscope sample excitation section 120 as shown in FIG. 3. The sample excitation section 120 uses many of the same components used in the sample excitation section 12 of FIG. 2. Therefore, in the interests of brevity, these components have been provided the same reference numerals, and an explanation of their function and operation will not be repeated.

The sample excitation section 120 differs from the sample excitation system 12 by incorporating the components of the sample excitation system 120 in a confocal microscope. The light from the excitation laser 14 is coupled to a partially reflective, partially transparent dichroic mirror, which acts as the beamsplitter 26. Some of the light from the beamsplitter 26 is directed through the path 20 to the fast photodiode detector 30 (FIG. 2) and processed as explained above. The remainder of the excitation light is reflected by the beamsplitter 26 through a microscope objective lens 124 onto the sample 50. Fluorescence from the sample 50 passes through the beamsplitter 26 and is reflected from a mirror 128 to a confocal pinhole 130. After passing through the pinhole 130, the fluorescence passes through an imaging lens 134 and is dispersed into its spectral components by the prism 56. The spectral components from the prism 56 are then processed as explained above with reference to FIG. 2. Using the sample excitation system 120 in the system 10 (FIG. 2) in place of the sample excitation system 12 therefore allows the wavelength and emission time of each detected fluorescence photon emitted from a microscopic sample to be determined and recorded. Further, the fluorescence spectrum and the wavelength dependent lifetime for each point in the image are simultaneously determined and recorded.

Although the present invention has been described with reference to the disclosed embodiments, persons skilled in the art will recognize that changes may be made in form and detail without departing from the spirit and scope of the invention. Such modifications are well within the skill of those ordinarily skilled in the art. Accordingly, the invention is not limited except as by the appended claims.

We claim:

1. A system for determining the wavelength and/or delay time of a photon emitted from a sample, the system comprising:
   an electromagnetic source emitting an excitation pulse;
   a first optical path coupling the excitation pulse to the sample so that the sample can emit a photon in response to the excitation pulse;
   a photon detector having a plurality of detector elements each of which generates an electrical pulse when a photon is incident on the detector element;
   a second optical path between the sample and the photon detector, the second optical path including a redirecting device operable to alter the second optical path as a function of the wavelength of the photon emitted from the sample so that the detector element of the photon detector receiving the photon is determined by the wavelength of the photon;
   at least one delay line having first and second output terminals at opposite ends and a plurality of taps between the output terminals, each of the taps being coupled to receive an electrical pulse from a respective detector element of the photon detector;
   a respective first timer coupled to the first output terminal of the at least one delay line, the respective first timer determining a first time corresponding to the lapse in time from the excitation pulse to receipt of a resulting electrical pulse at the first output terminal;

a respective second timer coupled to the second output terminal of the at least one delay line, the respective second timer determining a second time corresponding to the lapse in time from the excitation pulse to receipt of a resulting electrical pulse at the second output terminal; and a calculation device providing at least either an indication of the difference between the first and second times or an indication of the sum of the first and second times, the difference between the first and second times providing an indication of the wavelength of the emitted photon and the sum of the first and second times providing an indication of the emission delay of the emitted photon.

2. The system of claim 1 wherein the electromagnetic source comprises a laser so that the excitation pulse comprises a laser pulse.

3. The system of claim 1 wherein the redirecting device in the second optical path comprises a prism.

4. The system of claim 1 wherein the at least one delay line comprises N delay lines each of which is coupled to every $N^{th}$ detector element of the photon detector.

5. The system of claim 4 wherein the at least one delay line comprises 2 delay lines each of which is coupled to every other detector element of the photon detector.

6. The system of claim 1 wherein each of the first and second timers comprises:

a time-to-voltage converter generating a voltage that corresponds to the lapse in time from each excitation pulse to receipt of a resulting electrical pulse at the respective output terminal; and an analog-to-digital converter operable to generate a digital word corresponding to the amplitude of the voltage generated by the time-to-voltage converter.

7. The system of claim 6 wherein the time-to-voltage converter comprises:

a capacitor;
a constant current source; and
a switch coupling the constant current source to the capacitor, the switch being closed during a period corresponding to the time between the excitation pulse and receipt of a resulting electrical pulse at the respective output terminal.

8. The system of claim 7 wherein the switch is closed responsive to the excitation pulse and opened responsive to receipt of a resulting electrical pulse at the output terminal.

9. The system of claim 7 wherein the switch is closed responsive to receipt of a resulting electrical pulse at the output terminal and opened responsive to the excitation pulse.

10. The system of claim 1 wherein the first optical path comprises a beamsplitter dividing the excitation pulse into a first pulse that is incident on the sample and a second pulse that is incident on an excitation pulse detector for providing an indication of the occurrence of each of the excitation pulses.

11. The system of claim 10 wherein the excitation pulse detector comprises:

a photodiode receiving the second pulse and generating a corresponding electrical pulse; and a discriminator coupled to receive the electrical pulse from the photodiode, the discriminator being operable to generate at least one timing pulse from the electrical pulse.

12. The system of claim 1 wherein the calculation device is operable to provide both an indication of the difference between the first and second times and an indication of the sum of the first and second times.

13. The system of claim 1 wherein the calculation device comprises a digital computer.

14. The system of claim 1 wherein the electromagnetic source is operable to periodically emit excitation pulses.

15. The system of claim 14 wherein the signal propagation time through the at least one delay line is less than the period at which the excitation pulse is periodically emitted from the electromagnetic source.

16. The system of claim 1 wherein the photon detector comprises a photomultiplier tube, and the detector elements of the photon detector comprise anodes of the photomultiplier tube.

17. A confocal microscope, comprising:

a photon detection system for determining the wavelength and/or delay time of a photon emitted from a sample, the system comprising an electromagnetic source emitting an excitation pulse;

an objective lens positioned adjacent a sample;

a first optical path coupling the excitation pulse from the electromagnetic source and through the objective lens to the sample so that the sample can emit a photon in response to the excitation pulse;

a photon detector having a plurality of detector elements each of which generates an electrical pulse when a photon is incident on the detector element;

a second optical path between the sample and the photon detector, the second optical path including a redirecting device operable to alter the second optical path as a function of the wavelength of the photon emitted from the sample so that the detector element of the photon detector receiving the photon is determined by the wavelength of the photon;

at least one delay line having first and second output terminals at opposite ends and a plurality of taps between the output terminals, each of the taps being coupled to receive an electrical pulse from a respective detector element of the photon detector;

a respective first timer coupled to the first output terminal of the at least one delay line, the respective first timer determining a first time corresponding to the lapse in time from the excitation pulse to receipt of a resulting electrical pulse at the first output terminal;

a respective second timer coupled to the second output terminal of the at least one delay line, the respective second timer determining a second time corresponding to the lapse in time from the excitation pulse to receipt of a resulting electrical pulse at the second output terminal; and a calculation device providing at least either an indication of the difference between the first and second times or an indication of the sum of the first and second times, the difference between the first and second times providing an indication of the wavelength of the emitted photon and the sum of the first and second times providing an indication of the emission delay of the emitted photon.

18. The confocal microscope of claim 17 wherein the electromagnetic source comprises a laser so that the excitation pulse comprises a laser pulse.

19. The confocal microscope of claim 17 wherein the redirecting device in the second optical path comprises a prism.

20. The confocal microscope of claim 17 wherein the at least one delay line comprises N delay lines each of which is coupled to every $N^{th}$ detector element of the photon detector.

21. The confocal microscope of claim 20 wherein the at least one delay line comprises 2 delay lines each of which is coupled to every other detector element of the photon detector.

22. The confocal microscope of claim 17 wherein each of the first and second timers comprises:
   a time-to-voltage converter generating a voltage that corresponds to the lapse in time from each excitation pulse to receipt of a resulting electrical pulse at the respective output terminal; and
   an analog-to-digital converter operable to generate a digital word corresponding to the amplitude of the voltage generated by the time-to-voltage converter.

23. The confocal microscope of claim 22 wherein the time-to-voltage converter comprises:
   a capacitor;
   a constant current source; and
   a switch coupling the constant current source to the capacitor, the switch being closed during a period corresponding to the time between the excitation pulse and receipt of a resulting electrical pulse at the respective output terminal.

24. The confocal microscope of claim 17 wherein the first optical path comprises a beamsplitter dividing the excitation pulse into a first pulse that is incident on the sample and a second pulse that is incident on an excitation pulse detector for providing an indication of the occurrence of each of the excitation pulses.

25. The confocal microscope of claim 24 wherein the excitation pulse detector comprises:
   a photodiode receiving the second pulse and generating a corresponding electrical pulse; and
   a discriminator coupled to receive the electrical pulse from the photodiode, the discriminator being operable to generate at least one timing pulse from the electrical pulse.

26. The confocal microscope of claim 17 wherein the calculation device is operable to provide both an indication of the difference between the first and second times and an indication of the sum of the first and second times.

27. The confocal microscope of claim 17 wherein the electromagnetic source is operable to periodically emit excitation pulses, and wherein the signal propagation time through the at least one delay line is less than the period at which the excitation pulse is periodically emitted from the electromagnetic source.

28. The confocal microscope of claim 17 wherein the photon detector comprises a photomultiplier tube, and the detector elements of the photon detector comprise anodes of the photomultiplier tube.

29. A method of determining the wavelength and/or delay time of a photon emitted from a sample, the method comprising:
   directing an excitation pulse onto the sample so that the sample can emit a photon in response to the excitation pulse;
   directing the photon emitted from the sample along a path to locations corresponding to the wavelength of the photon;
   generating an electrical pulse at the location to which the photon is directed;
   propagating the electrical pulse from the location along first and second paths extending in opposite directions along a range of locations to which the photon can be directed corresponding to a range of wavelengths;
   determining a first time corresponding to the lapse in time from the excitation pulse being directed onto the sample to the electrical pulse propagating to a predetermined location along the first path;
   determining a second time corresponding to the lapse in time from the excitation pulse being directed onto the sample to the electrical pulse propagating to a predetermined location along the second path;
   and calculating at least either the difference between the first and second times or the sum of the first and second times, the difference between the first and second times providing an indication of the wavelength of the emitted photon and the sum of the first and second times providing an indication of the emission delay of the emitted photon.

30. The method of claim 29 wherein the excitation pulse comprises a laser pulse.

31. The method of claim 29 wherein the acts of determining the first and second times corresponding to the lapse in time from the excitation pulse being directed onto the sample to the electrical pulse propagating to a predetermined location along the first and second path, respectively, each comprise:
   providing a voltage that starts linearly increasing with time when the excitation pulse is directed onto the sample and stops linearly increasing when the electrical pulse had propagated to a predetermined location along the first path; and
   determining the magnitude of the voltage when the voltage stops linearly increasing.

32. The method of claim 29 wherein the act of calculating at least either the difference between the first and second times or the sum of the first and second times comprises calculating both the difference between the first and second times and the sum of the first and second times.

33. The method of claim 29 wherein the act of directing an excitation pulse onto the sample comprises periodically directing an excitation pulse onto the sample.

34. The method of claim 29 wherein the act of propagating the electrical pulse from the location along first and second paths comprises propagating the electrical pulse from the location along first and second paths for a duration that is less than the period at which the excitation pulses are periodically directed onto the sample.

35. The method of claim 29 wherein the act of directing the photon emitted from the sample along a path to locations corresponding to the wavelength of the photon comprises directing the photon to a photomultiplier tube having a plurality of anodes, and wherein the act of generating an electrical pulse at the location to which the photon is directed comprises generating an electrical pulse at the anode to which the photon is directed.

* * * * *